United States Patent [19]

Maillard et al.

[11] 4,325,954
[45] Apr. 20, 1982

[54] PYRROLOPYRIMIDINONES AND PYRROLOIMIDAZOLONES AND THEIR COMPOSITIONS AND THERAPEUTIC METHODS

[75] Inventors: Jacques G. Maillard, Versailles; Tri Vovan, Igny; Jacky M. Legeai, Palaiseau, all of France

[73] Assignee: Laboratoires Jacques Logeais, Issay les Moulineaux, France

[21] Appl. No.: 117,482

[22] Filed: Feb. 1, 1980

[30] Foreign Application Priority Data

Feb. 20, 1979 [FR] France ................... 79 04266

[51] Int. Cl.$^3$ ................ A61K 31/505; C07D 471/04; C07D 487/04
[52] U.S. Cl. ................ 424/251; 544/282; 548/302; 546/121; 424/258; 424/273 R; 424/274; 260/244.4; 260/326.37; 260/326.5 B
[58] Field of Search ................ 544/282; 424/251

[56] References Cited

U.S. PATENT DOCUMENTS

| | | | |
|---|---|---|---|
| 3,585,198 | 6/1971 | Meszards et al. | 544/282 |
| 3,929,787 | 12/1975 | Yale | 424/251 |
| 4,209,622 | 6/1980 | Meszards et al. | 424/251 |
| 4,219,649 | 8/1980 | Knoll et al. | 544/282 |

FOREIGN PATENT DOCUMENTS

| | | | |
|---|---|---|---|
| 4530M | 6/1965 | France | 544/282 |
| 4530 | 6/1965 | France . | |

*Primary Examiner*—Donald G. Daus
*Assistant Examiner*—Sharon A. Gibson

*Attorney, Agent, or Firm*—Young & Thompson

[57] ABSTRACT

The present invention relates to compounds having the formula:

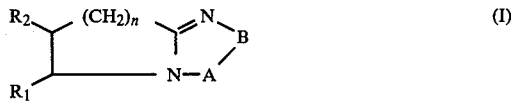

in which:
n is equal to 1 or 2,
$R_1$ represents a hydrogen atom and $R_2$ represents a phenyl group or a benzofuryl group; or $R_2$ represents a hydrogen atom and $R_1$ represents a phenyl group or a benzyl group; and
grouping -A-B- represents a group of the formula:

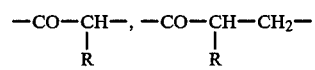

or —CO—$(CH_2)_3$— in which R represents a hydrogen atom, a $C_{1-6}$ alkyl radical, a phenyl group, a benzyl group, a methylthioethyl group, or a group having the formula —$(CH_2)_m$—COOR′ in which m is equal to 0, 1 or 2 and R′ is a $C_{1-6}$ alkyl radical,
and their pharmacologically acceptable acid addition salts.

These compounds are useful in the treatment of depressions.

4 Claims, No Drawings

PYRROLOPYRIMIDINONES AND PYRROLOIMIDAZOLONES AND THEIR COMPOSITIONS AND THERAPEUTIC METHODS

DESCRIPTION

This invention relates to new condensed pyrrolidine or piperidine derivatives, and to their therapeutic applications, typically as antidepressants.

French patent FR 4530 M discloses piperidino[1,2-a]imidazole derivatives which are free from aromatic substituents.

Said document mentions an action of the compounds on the central nervous system, which action, however, is either a depressant or a stimulant action, depending on the compounds, which could by no means suggest the application of all the compounds of this invention as antidepressants.

French patent FR 2,299,029 discloses 6-aryl-pyrrolo[1,2-a]imidazole derivatives which differ from the compounds of this invention by the absence of a carbonyl group in the imidazole moiety. In addition, said compounds are described as anti-hypertensive agents having a slight sedative effect, which could by no means suggest the application of the compounds of this invention.

Finally, French patent FR 7813 M describes homopyrimidazole derivatives which differ from the compounds of this invention by the absence of aromatic substituents on piperidine ring. In addition, said compounds are described as analgesic agents, which could by no means suggest the application of the compounds of this invention.

The present invention relates to compounds having the formula (I):

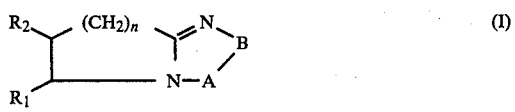

in which: n=1 or 2;
  $R_1$ represents a hydrogen atom and $R_2$ represents a phenyl group or a 2-benzofuryl group; or $R_2$ represents a hydrogen atom and $R_1$ represents a phenyl group or a benzyl group; and
  grouping -A-B- represents a group of the formula

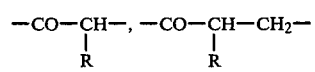

or $-CO-(CH_2)_3-$ in which R represents a hydrogen atom, a $C_{1-6}$ alkyl radical, a phenyl group, a benzyl group, a methylthioethyl group or a group of the formula $-(CH_2)_m-COOR'$ in which m=0, 1 or 2 and R' is a $C_{1-6}$ alkyl radical, and their pharmacologically acceptable acid addition salts.

The salts may typically be those formed with hydrochloric, sulfuric, phosphoric, methane-sulfonic, maleic, succinic, pamoic, acetic, fumaric, lactic, aspartic and citric acids.

The compounds of the formula (I) may be prepared by a process comprising reacting a compound of the formula (II):

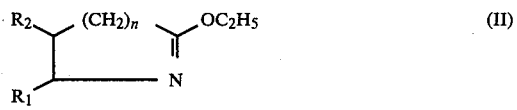

in which n, $R_1$ and $R_2$ have the aforesaid meanings, with an amine of the formula:

$$R''O-A-B-NH_2 \quad (III)$$

in which A and B have the aforesaid meanings and R'' represents a hydrogen atom or a $C_{1-6}$ alkyl radical, to give a compound having the formula:

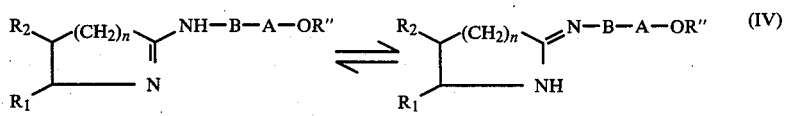

and then cyclizing the resulting compound of the formula (IV) to a compound of the formula (I).

The amine of the formula (III) may be used as the base or in salt form, such as the hydrochloride.

The reaction of the compound of the formula (II) with the amine of the formula (III) may be effected by boiling within a solvent such ethanol or isopropanol.

The cyclization of the compound of the formula (VI) may typically be effected by heating said compound as the base after evaporation of the solvent, with subsequent distillation under reduced pressure.

In some cases, this cyclization occurs spontaneously at room temperature.

The compound of the formula (IV) may also be boiled within an aqueous or alcoholic medium. Therefore, the intermediate isolation of the compound of the formula (IV) is not indispensable and the compound of the formula (I) may be obtained directly by heating the compound of the formula (II) with the compound of the formula (III) in salt form.

The following non limiting Examples illustrate the present invention.

EXAMPLE 1

Compound (I);

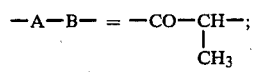

n=1; $R_1$=H; $R_2$=$C_6H_5$ (a) A solution of 9.45 g (0.05 mole) 2-ethoxy-4-phenyl-Δ1-pyrroline ((II), n=1; $R_1$=H; $R_2$=$C_6H_5$) and 7.7 g (DL)-ethyl-alaninate hydrochloride ((III);

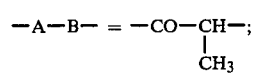

R''=$C_2H_5$) in 100 ml ethanol is refluxed for 24 hours. After evaporation to dryness and trituration of the residue with ethyl acetate, intermediate product (IV) (n=1;

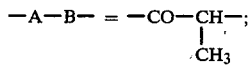

$R_1=H$; $R_2=C_6H_5$; $R''=C_2H_5$) is obtained in an amount of 12 g as the crystalline hydrochloride; m.p. (inst.)=139° C. (Yield: 81%).

(b) 11.6 g of the above derivative (IV) are dissolved in chloroform and converted to the base by stirring with excess saturated NaHCO$_3$ solution. After evaporation of the organic solvent, the residue is cyclized to the base (I) by heating, and is then slowly distilled under reduced pressure; b.p.$_{0.25}$=154° C. Product (I) crystallizes on cooling. M.p. (inst.)=65°-70° C. Yield: 65%.

(c) The same product (I) may be prepared from 2-ethoxy-4-phenyl-Δ1-pyrroline and DL-alanine ((III); R''=H) by refluxing within ethanol for 24 hours. After evaporation and addition of ether to the residue, intermediate derivative (IV) (R''=H) is obtained as a solid. M.p. (inst.)=231° C. Yield: 74%.

Thermal cyclization of derivative (IV), at about 200° C. under reduced pressure, leads to product (I) which distils and crystallizes on cooling.

EXAMPLE 2

Compound (I);

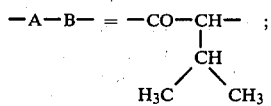

$n=1$; $R_1=H$; $R_2=C_6H_5$

The title compound is prepared in the same manner as the compound (I) of Example 1, from (DL)valine ((III);

—A—B— = —CO—CH—;
         |
         iC$_3$H$_7$

R''=H) and 2-ethoxy-4-phenyl-Δ1-pyrroline (II, n=1; $R_1=H$; $R_2=C_6H_5$).

Intermediate derivative (IV) is crystallized from ethyl acetate, and then from isopropanol. M.P. (inst.)=275°-280° C. Yield: 96%.

Derivative (IV) is cyclized to the base (I) by gradual heating at 250° C. under a pressure of 0.1 mm, followed by distillation. B.p.=152°-156° C. The product crystallizes on cooling. M.P. (inst.)=58° C. Yield: 73%.

EXAMPLE 3

Compound (I);

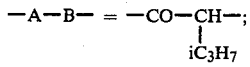

$n=1$; $R_1=H$; $R_2=C_6H_5$

This compound is prepared in the same manner as the compound (I) of Example 1, from (DL)ethyl-2-phenyl-2-aminoacetate((III);

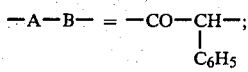

R''=C$_2$H$_5$) and 2-ethoxy-4-phenyl-Δ1-pyrroline ((II); n=1; $R_1=H$; $R_2=C_6H_5$). The intermediate product, obtained as the hydrochloride by evaporation of the solvent, is crystallized by trituration with ethyl acetate. M.P. (inst.)=206° C. Yield: 82%.

The preceding hydrochloride of derivative (IV) is transformed with ethanolic ammonia to the base which crystallizes spontaneously within 48 hrs. Base (I) crystallizes from ethanol. M.p.=194° C. Yield: 43%.

EXAMPLE 4

Compound (I);

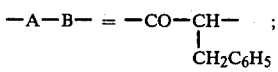

$n=1$; $R_1=H$; $R_2=C_6H_5$

The above compound is prepared in the same manner as the compound (I) of Example 1, from ethyl 2-amino-3-phenyl propionate hydrochloride ((III);

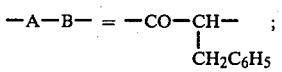

R''=C$_2$H$_5$) and 2-ethoxy-4-phenyl-Δ1-pyrroline ((II); n=1; $R_1=H$; $R_2=C_6H_5$). Intermediate product (IV), obtained as the hydrochloride by evaporation of the solvent, is crystallized from isopropanol. M.P. (inst.)=150° C.

Cyclization to the product (I) is effected by heating within a HCl-containing ethanolic solution.

The base is released by alkalinization, extracted with chloroform and distilled under reduced pressure. B.p.$_{0.2}$=208°-214° C. Overall yield: 34%.

EXAMPLE 5

Compound (I);

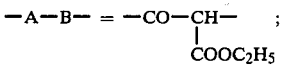

$n=1$; $R_1=H$; $R_2=C_6H_5$.

This compound is prepared in the same manner as compound (I) of Example 1, from ethyl amino-malonate hydrochloride ((III);

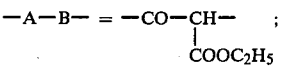

R''=C$_2$H$_5$) and 2-ethoxy-4-phenyl-Δ1-pyrroline ((II); n=1; $R_1=H$; $R_2=C_6H_5$). After evaporation of the solvent, the residue is taken up into chloroform, converted to the base by washing with excess saturated NaHCO$_3$ solution, and dried. After evaporation of the chloroform, the residue is crystallized by addition of ethyl acetate. M.p. (inst.)=215° C. (dec.). Yield: 53%.

EXAMPLE 6

Compound (I);

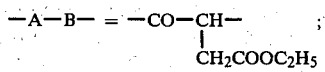

n=1; R₁=H; R₂=C₆H₅.

This compound is prepared in the same manner as the derivative (I) of Example 1, from ethyl 2-amino-succinate hydrochloride ((III);

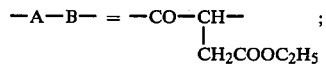

R″=C₂H₅) and 2-ethoxy-4-phenyl-Δ1-pyrroline. Without isolating derivative (IV), the desired base is obtained by evaporation of the solvent and alkalinization, and is distilled under reduced pressure; B.p.$_{0.5}$=220°–224° C. Yield: 39%.

EXAMPLE 7

Compound (I);

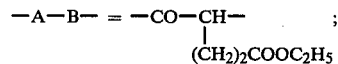

n=1; R₁=H; R₂=C₆H₅.

This compound is prepared in the same manner as the derivative (I) of Example 1, from ethyl glutamate hydrochloride ((III);

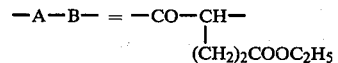

R″=C₂H₅) and 2-ethoxy-4-phenyl-Δ1-pyrroline.
Base: b.p.$_{0.2}$=204°–208° C. Yield: 28%.

EXAMPLE 8

Compound (I);

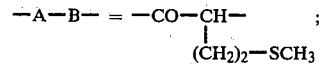

n=1; R₁=H; R₂=C₆H₅.

This compound is prepared in the same manner as the derivative (I) of Example 1, from methionine ethyl ester hydrochloride ((III);

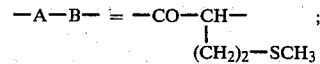

R″=C₂H₅) and 2-ethoxy-4-phenyl-Δ1-pyrroline.
Base: b.p.$_{0.3}$=208°–213° C. Yield: 37%.

EXAMPLE 9

Compound (I);

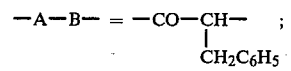

n=1; R₁=CH₂C₆H₅; R₂=H.

This compound is prepared in the same manner as the derivative (I) of Example 1, from ethyl 2-amino-3-phenyl-propionate hydrochloride ((III);

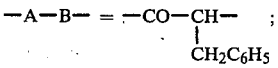

R″=C₂H₅) and 2-ethoxy-5-benzyl-Δ1-pyrroline ((II); n=1; R₁=CH₂C₆H₅; R₂=H). Intermediate product (IV) is obtained as an oily base, after evaporation of the solvent, alkalinisation and extraction with ether. Yield: 86%.

Crude derivative (IV) is cyclized by heating under reduced pressure; resulting product (I) is distilled.
B.p.$_{0.1}$=200° C. Yield: 45%.

EXAMPLE 10

Compound (I);

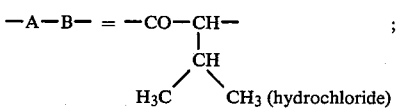

n=2; R₁=H; R₂=C₆H₅.

This compound is prepared in the same manner as the derivative (I) of Example 1, from (DL)valine ((III);

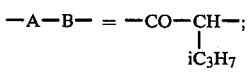

R″=H) and 2-ethoxy-5-phenyl-3,4,5,6-tetrahydropyridine ((II); n=2; R₁=H; R₂=C₆H₅). The base obtained by evaporation of the solvent is converted to the hydrochloride with a solution of HCl in isopropanol.
M.p. (inst.)=191°–193° C. Yield: 37%.

EXAMPLE 11

Compound (I)

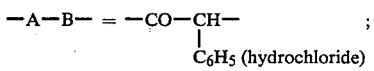

n=2; R₁=H; R₂=C₆H₅.

This compound is prepared in the same manner as the derivative (I) of Example 1, from 2-amino-2-phenyl-acetic acid ((III);

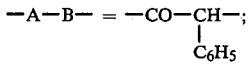

R″=H) and 2-ethoxy-5-phenyl-3,4,5,6-tetrahydro-pyridine ((II); n=2; R₁=H; R₂=C₂H₅). After refluxing within ethanol and cooling, intermediate derivative (IV) is filtered off and cyclized by heating in acetic acid at the boiling temperature for a period of time of 8 hours. Evaporation of the acetic acid leaves a residue which is taken up into an ethanolic HCl solution, in the hot; the hydrochloride of derivative (I) crystallizes in the cold. M.p. (inst.)=250°–255° C. (dec.). Yield: 30%.

EXAMPLE 12

Compound (I);

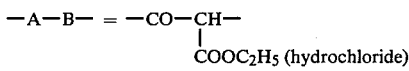

n=2; $R_1$=H; $R_2$=$C_6H_5$.

This compound is prepared in the same manner as the derivative (I) of Example 1, from ethyl aminomalonate hydrochloride ((III));

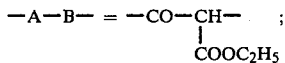

R"=$C_2H_5$) and 2-ethoxy-5-phenyl-3,4,5,6-tetrahydropyridine ((II); n=2; $R_1$=H; $R_2$=$C_6H_5$). The hydrochloride is crystallized from ethanol-isopropyl oxide. M.p. (inst.)=224° C. Yield: 42%.

EXAMPLE 13

Compound (I);

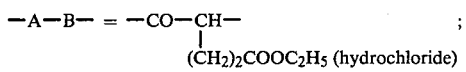

n=2; $R_1$=H; $R_2$=$C_6H_5$.

This compound is prepared in the same manner as the derivative (I) of Example 1, from ethyl glutamate hydrochloride ((III));

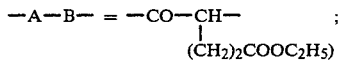

R"=$C_2H_5$) and 2-ethoxy-5-phenyl-3,4,5,6-tetrahydropyridine ((II); n=2; $R_1$=H; $R_2$=$C_6H_5$). Base (I) (b.p.$_{0.05}$=205°–215° C.) is converted to the hydrochloride which is crystallized from isopropanol. M.p. (inst.)=168°–170° C.

EXAMPLE 14

Compound (I) —A—B—=—CO—$CH_2CH_2$—; n=1; $R_1$=H; $R_2$=$C_6H_5$.

This compound is prepared in the same manner as the derivative (I) of Example 1, from 3-aminopropionic acid ((III); —A—B—=—CO—$CH_2$—$CH_2$—; R"=H) and 2-ethoxy-4-phenyl-Δ1-pyrroline. Intermediate product (IV) (R"=H) is obtained by evaporation of the solvent and crystallization from isopropanol. M.p. (inst.)=215° C. Yield: 70%.

Derivative (IV) is cyclized by heating at 180°–200° C. under reduced pressure, and is then distilled (b.p.$_{0.5-1}$=180°–210° C.) and crystallized from isopropyl ether. M.p. (inst.)=99° C. Yield: 72%.

EXAMPLE 15

Compound (I); —A—B—=—CO—$CH_2CH_2$—; n=1; $R_1$=H;

$R_2$ = 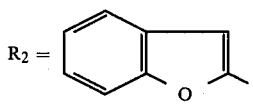

This compound is prepared in the same manner as the derivative (I) of Example 1, from 3-amino-propionic acid ((III); —A—B—=—CO—$CH_2CH_2$—; R"=H) and 2-ethoxy-4-(2-benzofuryl)-Δ1-pyrroline. After refluxing for 20 hours, the ethanol is evaporated off and the residue is distilled under reduced pressure. B.p.$_{0.4}$=202°–208° C. M.p. (inst.)=120° C. Yield: 69%.

EXAMPLE 16

Compound (I);

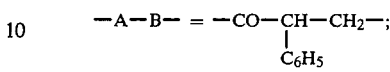

n=1; $R_1$=H; $R_2$=$C_6H_5$.

This compound is prepared in the same manner as the derivative (I) of Example 1 from ethyl 2-phenyl-3-amino-propionate hydrochloride ((III));

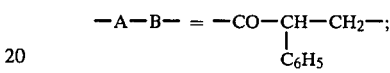

R"=$C_2H_5$) and 2-ethoxy-4-phenyl-Δ1-pyrroline.

The base is crystallized from ethyl acetate.

M.p. (inst.)=164° C. Yield=50%.

EXAMPLE 17

Compound (I); —A—B—=—CO—$CH_2CH_2$—; n=1; $R_1$=$C_6H_5$; $R_2$=H. This compound is prepared in the same manner as the derivative (I) of Example 1, from 3-amino-propionic acid ((III); —A—B—=—CO—$CH_2$—$CH_2$—; R"=H) and 2-ethoxy-5-phenyl-Δ1-pyrroline ((II); n=1; $R_1$=$C_6H_5$; $R_2$=H). Intermediate product (IV) is recrystallized from methanol.

M.p. (inst.)=178° C. Yield: 45%.

Derivative (IV) is cyclized by heating at about 200° C. under reduced pressure. Resulting product (I) is distilled (b.p.$_{0.2-0.3}$=154°–156° C.). Yield: 74%.

EXAMPLE 18

Compound (I); —A—B—=—CO—$CH_2CH_2CH_2$—; n=1; $R_1$=H; $R_2$=$C_6H_5$.

This compound is prepared in the same manner as the derivative (I) of Example 1, from 4-amino-butyric acid ((III); —A—B—=—CO—$CH_2$—$CH_2$—$CH_2$—; R"=H) and 2-ethoxy-4-phenyl-Δ1-pyrroline. After evaporation of the solvent, intermediate derivative (IV) is crystallized from isopropanol.

M.p. (inst.)=200° C. Yield: 73%.

Derivative (IV) is cyclized by heating at 200° C. under reduced pressure and resulting product (I) is distilled.

B.p.$_{0.1}$=162°–166° C. Yield: 11%.

The compounds of the formula (I) exhibit useful pharmacological properties, typically in the domain of the central nervous system, as non-anticholinergic antidepressants. Their toxicity appears only at dosages highly superior to the pharmacological active dosages, which makes them therapeutically useful for the treatment of depressive conditions, without the detrimental side-effects of the conventional antidepressants.

Results of toxicological and pharmacological investigations which demonstrate said properties are given below.

(a) Acute toxicity in mice

Each compound was administered orally or intraperitoneally as a single dose. The behavior of the test animals and the death rate were observed for several hours after the treatment, and then daily for at least one week.

The results obtained are reported in the following Table.

(b) Antidepressant activity

The antidepressant activity of each compound was evaluated in mice from its ability to antagonize palpebral ptosis induced by a reserpine injection. The different materials were administered orally, as a preventive treatment, one hour prior to intraperitoneal injection of reserpine (2 mg/kg). The intensity of the palpebral ptosis was then recorded at hourly intervals, for a period of time of 3 hours, according to a semi-quantitative scale (Rubin's scale). The test materials were administered at several dosage levels and, for most of them, the 50% efficient dosage ($ED_{50}$) which inhibits palpebral ptosis by a factor of 50% could be evaluated.

The results obtained are given in the following Table.

| Compound of example No. | $LD_{50}$ po (mg/kg) | $LD_{50}$ ip (mg/kg) | ptosis reserpine |
|---|---|---|---|
| 1 | >200 | >200 | $ED_{50} \simeq$ 33mg/kg |
| 2 | >200 | >200 | $ED_{50} >$ 30mg/kg |
| 3 | >200 | >200 | $ED_{50} \simeq$ 30mg/kg |
| 4 | >200 | <200 | $ED_{50} <$ 30mg/kg |
| 5 | >200 | >200 | $ED_{50} \simeq$ 7mg/kg |
| 6 | >>200 | >>200 | $ED_{50} \simeq$ 100mg/kg |
| 7 | >>200 | >>200 | $ED_{50} \simeq$ 30mg/kg |
| 8 | >>200 | >>200 | $ED_{50} \simeq$ 30mg/kg |
| 10 | >200 | >200 | $ED_{50} \simeq$ 100mg/kg |
| 12 | >200 | >200 | $ED_{50} \simeq$ 30mg/kg |
| 13 | >200 | >200 | $ED_{50} \simeq$ 30mg/kg |
| 14 | >>200 | >>200 | $ED_{50} =$ 5mg/kg |
| 15 | >200 | >200 | $ED_{50} \simeq$ 33mg/kg |
| 17 | >200 | >200 | $ED_{50} <$ 100mg/kg |
| 18 | >200 | >200 | $ED_{50} <<$ 33mg/kg |

(c) Atropine activity

In view of the detrimental atropine-like side-effect of the conventional antidepressants, this potential property was systematically investigated in the compounds of the formula (I).

The different materials were administered orally 60 minutes prior to subcutaneous oxotremorine injection at a dosage of 2 mg/kg.

15 minutes, and then 30 and 45 minutes after injection of the cholinergic agent, the various symptoms reflecting a parasympathetic stimulation were evaluated according to a semi-quantitative arbitrary scale (from 0 to 4).

peripheral cholinergic stimulation symptoms: tearfulness, salivation;

central cholinergic stimulation: trembling, Straub's phenomenon.

Almost all the compounds tested under such conditions have no modifying effect on the peripheral and central cholinergic effects of oxotremorine; a single compound exhibits a slight inhibitor activity at the dosage of 100 mg/kg (Example No. 10).

(d) Effects on the cardiovascular system

The compounds of the formula (I) were administered intravenously in dogs, at dosages from 0.1 mg/kg to 10 mg/kg. The changes of blood pressure, of the femoral arterial rate, of vascular resistance subsequent to said injections were recorded.

Most tests compounds do not exert any action on the blood pressure; a single of those is slightly vasoconstrictive (Example No. 5), and two others have a slight hypotensive action (Examples No. 6 and 8).

The absence of effects on the blood pressure noted with most said compounds makes it possible to exclude a sympathomimetic activity in the compounds of the formula (I).

The compounds of the formula (I) are therapeutically useful in the treatment of depressive syndromes and of cerebral infarction and are free from the usual detrimental side-effects of the products belonging to this therapeutic class (atropine-like effects, effects on blood pressure).

Said compounds may be administered to humans by the oral or rectal routes, as the free bases or in salt form (formulated as tablets, capsules, drops or suppositories), or parenterally (formulated as aqueous solutions of water-soluble salts) or in a galenic form insuring a programmed resorption.

The various formulations may contain 10–1000 mg active ingredient per unit dosage for oral and rectal administration, and 1–500 mg active ingredient for the other routes of administration. The daily dosage regimen may vary from 10 mg to 5 g, depending on the route of administration and the therapeutic applications contemplated.

Having now described our invention what we claim as new and desire to secure by Letters Patent is:

1. A compound selected from the group consisting of compounds of the formula:

$$\begin{array}{c} R_2 \diagdown \phantom{x} CH_2 \diagdown \phantom{x} N \diagdown \\ \phantom{xxxxxxxxxxx} B \\ R_1 \diagup \phantom{xxxxxx} - N - A \diagup \end{array} \quad (I)$$

in which:

$R_1$ is hydrogen and $R_2$ is selected from phenyl and benzofuryl or $R_2$ is hydrogen and $R_1$ is selected from phenyl and benzyl; and group —A—B— is —CO—CHR—CH$_2$— in which R is selected from hydrogen, $C_{1-6}$ alkyl, phenyl, benzyl, methylthioethyl and —(CH$_2$)$_m$—COOR' in which m is selected from 0, 1 and 2 and R' is $C_{1-6}$ alkyl, and a pharmacologically acceptable acid addition salt thereof.

2. Compound as claimed in claim 1, wherein $R_1$ is hydrogen, $R_2$ is phenyl and —A—B— is —CO—CH$_2$—CH$_2$—.

3. A therapeutic composition having an anti-depressant activity on the central nervous system containing an antidepressant effective amount of a compound as in claim 1 and a therapeutically acceptable excipient.

4. Process for the treatment of depression which comprises administering to a human in need thereof a therapeutic composition containing an antidepressant effective amount of a compound as in claim 1.

* * * * *